United States Patent [19]

Doxsey

[11] Patent Number: 5,861,260
[45] Date of Patent: Jan. 19, 1999

[54] DIAGNOSTIC METHODS FOR SCREENING PATIENTS FOR SCLERODERMA

[75] Inventor: Stephen J. Doxsey, Worcester, Mass.

[73] Assignee: University of Massachusetts, Boston, Mass.

[21] Appl. No.: 743,200

[22] Filed: Nov. 5, 1996

[51] Int. Cl.[6] .......................... C12Q 1/00; G01N 33/564
[52] U.S. Cl. .............. 435/7.1; 435/4; 435/7.21; 435/7.95; 435/960; 436/63; 436/506; 436/508; 436/518; 436/536
[58] Field of Search ................................ 435/4, 7.1, 7.95, 435/960; 436/63, 506, 508, 518, 536

[56] References Cited

U.S. PATENT DOCUMENTS

| 4,499,183 | 2/1985 | Sujansky et al. | 435/6 |
| 5,196,307 | 3/1993 | Earnshaw et al. | 435/7.9 |
| 5,296,383 | 3/1994 | Himeno et al. | 436/507 |

OTHER PUBLICATIONS

Blomberg et al, Molec. Biol. of the Cell, 7, Suppl., 205A, 1996.
Balczon et al., "The Identification of Mammalian Centrosmal Antigens Using Human Autoimmune Anticentrosome Antisera", Cell Motility and Cytoskeleton 20:121–135, 1991.
Archer et al., "Deconstructing the Microtubule–Organizing Center", Cell 76:589–591, 1994.
Calarco–Gilliam, "Centrosome Development in Early Mouse Embryos as Defined by an Autoantibody Against Pericentriolar Material", Cell 35:621–629, 1983.
Clayton et al., "Microtubule Nucleating Sites in Higher Plant cells Identified by an Auto–Antibody Against Perticentriolar Material", Cell Biol. 101:319–324, 1985.
Doxsey et al., Pericentrin, pp. 118–119, in Guidebook to the Cytoskeletal and Motor Protein (Kreis et al., eds., Oxford University Press, Oxford, 1993.
Doxsey et al., "Pericentrin, a Centrosome Protein Involved in the Organization of Microtubules in Meiosis and Mitosis", J.Cell Biol. 111:172a, Abstract 998, 1991.
Doxsey et al., "Pericentrin, a Highly Conserved Centrosome Protein Involved in Microtubule Organization", Cell 76:639–650, 1994.
Doxsey et al., "A Centrosome Protein Involved in Meiotic Spindle Formation", J. Cell Biology 111:179a, Abstract 990, 1990.
Kalt et al., "Molecular Components of the Centrosome", Trends in Cell Biology, 3:118–128, 1993.
Kellogg et al., "The Centrosome and Cellular Organization", Annual Review of Biochem., 63:639–674, 1994.
Nakamura et al., "Improvement of Assays for Detecting Auto Antibodies", J. Clin. Lab. Anal., 8:360, 1994.
Sato et al., "Antihistone Antibodies in Patients with Localized Scleroderma", Arthritis and Rheumatism 36:1137–1141, 1993.
Shero et al., "High Titers of Autoantibodies to Topoisomerase I (Sc1–70) in Sera from Scleroderma Patients", Science 231:737–740, 1986.
Stearns et al., "In Vitro Reconstitution of Centrosome Assembly and Function: The Central Role γTubulin", Cell, 76:623–637, 1994.
Tuffanelli et al., "Anticentromere and Anticentriole in the Scleroderma Spectrum", Arch Dermatol. 119:560–566, 1983.
Vazquez–Abad et al., "Longitudinal Study of Anticentromere and Antitopoisomerase–I Isotypes", Clin. Immunol. and Immunopath. 74:257–270, 1995.
Vidair et al., "Heat Shock Alters Centrosome Organization Leading to Mitotic Dysfunction and Cell Death", J. Cell. Physiology 154:443–455, 1993.
International Search Report mailed Feb. 23, 1998.

*Primary Examiner*—David Saunders
*Attorney, Agent, or Firm*—Fish & Richardson P.C.

[57] ABSTRACT

Disclosed are diagnostic methods for screening a patient for sclerotic disease. One diagnostic method includes obtaining a biological sample from the patient; obtaining a substantially pure CP140 polypeptide fragment; contacting the sample with the CP140 polypeptide; and detecting patient autoantibody:CP140 complexes as an indication of the presence of sclerotic disease in the patient. Other methods of screening patients for scleroderma are also described.

10 Claims, 8 Drawing Sheets

```
                              10          20          30
                              |           |           |
SEQ ID NO:  1    GATAGACAGG  AGGCTTTTGA  GAGATTCAGT
SEQ ID NO:  2     D  R  Q    E  A  F  E   R  F  S
SEQ ID NO:  3    ATCAGAGTAT  GCTGAAATTG  ATAAAGCCCC
SEQ ID NO:  4     S  E  Y    A  E  I     D  K  A  P
SEQ ID NO:  5    GAAAAAAAAT  AAGTGCCGCC  CCAACTCGAC
SEQ ID NO:  6     K  K  I    S  A  A     P  T  R
SEQ ID NO:  7    AAGAGCGGTA  AAGAACAACA  GCTTGACATT
SEQ ID NO:  8     K  S  G    K  E  Q  Q   L  D  I
SEQ ID NO:  9    AAATGAAGCC  CTGAAGAAGG  ATTTAGAAGG
SEQ ID NO: 10     N  E  A    L  K  K     D  L  E  G
SEQ ID NO: 11    AAGTGCCCTC  CAAGAGCAGC  ATGAGGTGAA
SEQ ID NO: 12     S  A  L    Q  E  Q     H  E  V  N
SEQ ID NO: 13    AAACTGAAAT  TAGGAACTGG  GGAAATGAAC
SEQ ID NO: 14     K  L  K    L  G  T  G   E  M  N 40          50          60
                              |           |           |
SEQ ID NO:  1    TTAGAAGAGG  TAGAAAGACT  GGAAAGAGAC
SEQ ID NO:  2     L  E  E    V  E  R  L   E  R  D
SEQ ID NO:  3    AGATGAAAGC  CCTTACATTG  GCAA
SEQ ID NO:  4     D  E  S    P  Y  I     G
SEQ ID NO:  5    TATCCGAACT  GCCTGATGAA  ATAGAAAAGG
SEQ ID NO:  6     L  S  E  L  P  D  E    I  E  K
SEQ ID NO:  7    ATGAACAAGC  AGTACCAACA  ACTTGAAAGT
SEQ ID NO:  8     M  N  K    Q  Y  Q  Q   L  E  S
SEQ ID NO:  9    TGTTATCAGT  GGGTTGCAAG  AATACCTGGG
SEQ ID NO: 10     V  I  S    G  L  Q     E  Y  L  G
SEQ ID NO: 11    TGCATCTTTG  CAGCAGACCC  AGGGAGATCT
SEQ ID NO: 12     A  S  L    Q  Q  T     Q  G  D  L
SEQ ID NO: 13    ATCCATAGTC  CTTCAGATGT  CTTAGGGAAA
SEQ ID NO: 14     I  H  S    P  S  D  V   L  G  K 70          80          90
                              |           |           |
SEQ ID NO:  1    CTAGAAAAAA  AGATGATAGA  AACTGAAGAG
SEQ ID NO:  2     L  E  K    K  M  I  E   T  E  E
SEQ ID NO:  3    <==
SEQ ID NO:  4    <==
SEQ ID NO:  5    CCGAACCACC  AATTTTGAGA  GCTACTGAAG
SEQ ID NO:  6     A  E  P  P  I  L  R    A  T  E
SEQ ID NO:  7    CGTTTGGATG  AGATACTTTC  TAGAATTGCT
SEQ ID NO:  8     R  L  D    E  I  L  S   R  I  A
SEQ ID NO:  9    GACCATTAAA  GGCCAGGCAA  CTCAGGCCCA
SEQ ID NO: 10     T  I  K    G  Q  A     T  Q  A  Q
SEQ ID NO: 11    CAGTGCCTAT  GAAGCTGAGC  TAGAGGCTCG
SEQ ID NO: 12     S  A  Y    E  A  E     L  E  A  R
SEQ ID NO: 13    AGTCTTGCTG  ATTTACAGAA  ACAATTCAGT
SEQ ID NO: 14     S  L  A    D  L  Q  K   Q  F  S
```

FIG. 1A

```
                              100         110.        120
                               |           |           |
SEQ ID NO:  1    CTTAAGAGCA AACAAACAAG GTTCCTTGAG
SEQ ID NO:  2      L K S      K Q T R     F L E
SEQ ID NO:  3    <==
SEQ ID NO:  4    <==
SEQ ID NO:  5    AATTTAAACA ACTGGAAGAA GCTATACCAC
SEQ ID NO:  6      E F K Q    L E E       A I P
SEQ ID NO:  7    AAGGAAACGG AAGAGATTAA GGACCTTGAA
SEQ ID NO:  8      K E T      E E I K     D L E
SEQ ID NO:  9    GAATGAGTGC AGGAAGCTGC GGG
SEQ ID NO: 10      N E C      R K L       R
SEQ ID NO: 11    GCTAAACCTA AGGGATGCTG AAGCCAACCA
SEQ ID NO: 12      L N L      R D A       E A N Q
SEQ ID NO: 13    GAAATTCTTG CACGCTCCAA GTGGGAAAGA
SEQ ID NO: 14      E I L      A R S K     W E R 130         140         150
                               |           |           |
SEQ ID NO:  1    GAAATTAAAA ATCAAGATAA ATTGAATAAA
SEQ ID NO:  2      E I K      N Q D K     L N K
SEQ ID NO:  3    <==
SEQ ID NO:  4    <==
SEQ ID NO:  5    TAAAAAGAT TTCAGAAGCA GGGAAAGACC
SEQ ID NO:  6      L K K I    S E A       G K D
SEQ ID NO:  7    GAACAGCTTA CTGAAGGCCA GATAGC
SEQ ID NO:  8      E Q L      T E G Q     I
SEQ ID NO:  9    <==
SEQ ID NO: 10    <==
SEQ ID NO: 11    GCTCAAGGAA AAGTTGGAAA AAGTAACAAG
SEQ ID NO: 12      L K E      K L E       K V T R
SEQ ID NO: 13    GATGAAGCAC AAGTTAGAGA GAGAAAACTC
SEQ ID NO: 14      D E A      Q V R E     R K L 160         170         180
                               |           |           |
SEQ ID NO:  1    TCATTAAAAG AGGAGGCCAT GTTACAGAAA
SEQ ID NO:  2      S L K      E E A M     L Q K
SEQ ID NO:  3    <==
SEQ ID NO:  4    <==
SEQ ID NO:  5    TTCTTTACAA GCAGTTGAGT GGTAGACTAC
SEQ ID NO:  6      L L Y K    Q L S       G R L
SEQ ID NO:  7    <==
SEQ ID NO:  8    <==
SEQ ID NO:  9    <==
SEQ ID NO: 10    <==
SEQ ID NO: 11    ACTTACCCAG TTAGAACAAT CAGCCCTTCA
SEQ ID NO: 12      L T Q      L E Q       S A L Q
SEQ ID NO: 13    CAAGAAGAAA TGGCTCTGCA GCAAGAGAAA
SEQ ID NO: 14      Q E E      M A L Q     Q E K
```

FIG. 1B

```
                        190          200         210
                        |            |           |
SEQ ID NO:  1   CAGAGCTGTG AGGAACTCAA GAGTGACTTA
SEQ ID NO:  2    Q  S  C   E  E  L  K    S  D  L
SEQ ID NO:  3   <==
SEQ ID NO:  4   <==
SEQ ID NO:  5   AACTTGTAAA TAAATTACGC CAGGAAGCTC
SEQ ID NO:  6    Q  L  V  N   K  L  R    Q  E  A
SEQ ID NO:  7   <==
SEQ ID NO:  8   <==
SEQ ID NO:  9   <==
SEQ ID NO: 10   <==
SEQ ID NO: 11   AGCAGAACTT GAGAAGGAAA GGCAAGCCCT
SEQ ID NO: 12     A  E  L   E  K  E    R  Q  A  L
SEQ ID NO: 13   CTGGCAACTG GACAAGAAGA GTTCAGGCAG
SEQ ID NO: 14    L  A  T   G  Q  E  E    F  R  Q 220          230         240
                        |            |           |
SEQ ID NO:  1   AACACAAAAA ATGAATTGCT AAAACAGAAG
SEQ ID NO:  2    N  T  K   N  E  L  L    K  Q  K
SEQ ID NO:  3   <==
SEQ ID NO:  4   <==
SEQ ID NO:  5   TGGATCTAGA ACTGCAGATG GAAAAGCAAA
SEQ ID NO:  6    L  D  L  E   L  Q  M    E  K  Q
SEQ ID NO:  7   <==
SEQ ID NO:  8   <==
SEQ ID NO:  9   <==
SEQ ID NO: 10   <==
SEQ ID NO: 11   CAAGAATGCC CTTGGAAAAG CCCAGTTCTC
SEQ ID NO: 12     K  N  A   L  G  K    A  Q  F  S
SEQ ID NO: 13   GCCTGTGAGA GAGCCCTG
SEQ ID NO: 14    A  C  E   R  A  L 250          260         270
                        |            |           |
SEQ ID NO:  1   ACCATAGAAT TAACACGAGC ATGTCAGAAG
SEQ ID NO:  2    T  I  E   L  T  R  A    C  Q  K
SEQ ID NO:  3   <==
SEQ ID NO:  4   <==
SEQ ID NO:  5   AGCAGGAAAT TGCCGGAAAG CAGAAGGAGA
SEQ ID NO:  6    K  Q  E  I   A  G  K    Q  K  E
SEQ ID NO:  7   <==
SEQ ID NO:  8   <==
SEQ ID NO:  9   <==
SEQ ID NO: 10   <==
SEQ ID NO: 11   AGAAGAAAAG GAGCAAGAGA ACAGTGAGCT
SEQ ID NO: 12     E  E  K   E  Q  E    N  S  E  L
SEQ ID NO: 13   <==
SEQ ID NO: 14   <==
```

FIG. 1C

```
                                    280         290         300
                                    |           |           |
SEQ ID NO:  1  CAATATGAGC TGGAACAGGA ATTGGCCTTT
SEQ ID NO:  2   Q  Y  E   L  E  Q  E   L  A  F
SEQ ID NO:  3  <==
SEQ ID NO:  4  <==
SEQ ID NO:  5  TTAAGGACCT GCAAATAGCC ATAGATAGCC
SEQ ID NO:  6   I  K  D  L   Q  I  A   I  D  S
SEQ ID NO:  7  <==
SEQ ID NO:  8  <==
SEQ ID NO:  9  <==
SEQ ID NO: 10  <==
SEQ ID NO: 11  CCATGCAAAA CTTAAACACT TGCAGGATGA
SEQ ID NO: 12    H  A  K   L  K  H   L  Q  D  D
SEQ ID NO: 13  <==
SEQ ID NO: 14  <==

310         320         330
                                    |           |           |
SEQ ID NO:  1  TATAAAATTG ATGCT
SEQ ID NO:  2   Y  K  I   D  A
SEQ ID NO:  3  <==
SEQ ID NO:  4  <==
SEQ ID NO:  5  TGGATTCCAA AGACCCAAAA CATTCCCATA
SEQ ID NO:  6   L  D  S  K   D  P  K   H  S  H
SEQ ID NO:  7  <==
SEQ ID NO:  8  <==
SEQ ID NO:  9  <==
SEQ ID NO: 10  <==
SEQ ID NO: 11  CAATAATCTG TTAAAACAGC AACTTAAAGA
SEQ ID NO: 12    N  N  L   L  K  Q   Q  L  K  D
SEQ ID NO: 13  <==
SEQ ID NO: 14  <==

340         350         360
                                    |           |           |
SEQ ID NO:  1  <==
SEQ ID NO:  2  <==
SEQ ID NO:  3  <==
SEQ ID NO:  4  <==
SEQ ID NO:  5  <==
SEQ ID NO:  6  <==
SEQ ID NO:  7  <==
SEQ ID NO:  8  <==
SEQ ID NO:  9  <==
SEQ ID NO: 10  <==
SEQ ID NO: 11  TTTCCAGAAT CACCTTAACC ATGTGGTTGA
SEQ ID NO: 12   F  Q  N   H  L  N   H  V  V  D
SEQ ID NO: 13  <==
SEQ ID NO: 14  <==
```

FIG. 1D

| Primer | | Primer sequence 5'-3' |
|---|---|---|
| 1. R2.5' 324-345 | SEQ ID NO: 15 | CGA GCA TGT CAG AAG CAA TAT G |
| 2. R2.5' 424-442 | SEQ ID NO: 16 | CCC AGA TGA AAG CCC TTA C |
| 3. R2.5' 434-453 | SEQ ID NO: 17 | AGC CCT TAC ATT GGC AAA TC |
| 4. R2.5' 535-555 | SEQ ID NO: 18 | CAG GCA GTA CAG ATC AAG AAG |
| 5. R2.5' 564-583 | SEQ ID NO: 19 | GAA CTT GAG AGG CCA CAC AC |
| 6. R2.5' 878-897 | SEQ ID NO: 20 | TAA ATT ACG CCA GGA ACG TC |
| 7. R2.5' 1089-1108 | SEQ ID NO: 21 | GCC AGA TAG CAG CAA AATG AAG |
| 8. R2. 5' PCR 60-41 | SEQ ID NO: 22 | TAC TGG CTG ACC TTC CAA AC |
| 9. R2.5' PCR 84-63 | SEQ ID NO: 23 | AGC CTC CTG TCT ATC CTG AGT G |
| 10. R2. 5' PCR 129-106 | SEQ ID NO: 24 | GTC TCT TTC CAG TCT TTC TAC CTC |
| 11. R2.3' 224-242 | SEQ ID NO: 25 | CTT CTT AGC TCA TCC ACA C |
| 12. R2.3' 291-309 | SEQ ID NO: 26 | GAA CCA AAC CAT CAA CCA C |
| 13. R2.3' 483-504 | SEQ ID NO: 27 | GAA GGG CTG ATT GTT CTA ACT G |
| 14. R2.3'661-681 | SEQ ID NO: 28 | TTC TAG CTC TGC AAG CTC CTC |
| 15. R2.3' 724-746 | SEQ ID NO: 29 | ACT TTC TAG CTC TGC AAG CTC C |
| 16. R2.3'843-863 | SEQ ID NO: 30 | CAA CCC ACT GAT AAC ACC TTC |
| 17. R2.3'1011-1032 | SEQ ID NO: 31 | GTC AAG CTG TTG TTC TTT ACC G |
| 18. R2.3' PCR 69-49 | SEQ ID NO: 32 | GGA CAA GAA GAG TTC AGG CAG |
| 19. R2.3' PCR 72-52 | SEQ ID NO: 33 | ACT GGA CAA GAA GAG TTC AGG |
| 20. R2.3' PCR 112-92 | SEQ ID NO: 34 | ACT CCA AGA AGA AAT GGC TC |
| 21. HA-R2.92-115 | SEQ ID NO: 35 | GAG GTA GAA AGA CTG GAA AGA GAC |
| 22. R2.3'. 68-87 | SEQ ID NO: 36 | TGC CTG AAC TCT TCT TGT CC |

FIG. 3

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 1...315

( x i ) SEQUENCE DESCRIPTION: SEQ ID NO:1:

```
GAT  AGA  CAG  GAG  GCT  TTT  GAG  AGA  TTC  AGT  TTA  GAA  GAG  GTA  GAA  AGA        48
Asp  Arg  Gln  Glu  Ala  Phe  Glu  Arg  Phe  Ser  Leu  Glu  Glu  Val  Glu  Arg
 1                  5                        10                       15

CTG  GAA  AGA  GAC  CTA  GAA  AAA  AAG  ATG  ATA  GAA  ACT  GAA  GAG  CTT  AAG        96
Leu  Glu  Arg  Asp  Leu  Glu  Lys  Lys  Met  Ile  Glu  Thr  Glu  Glu  Leu  Lys
                20                        25                       30

AGC  AAA  CAA  ACA  AGG  TTC  CTT  GAG  GAA  ATT  AAA  AAT  CAA  GAT  AAA  TTG       144
Ser  Lys  Gln  Thr  Arg  Phe  Leu  Glu  Glu  Ile  Lys  Asn  Gln  Asp  Lys  Leu
           35                        40                       45

AAT  AAA  TCA  TTA  AAA  GAG  GAG  GCC  ATG  TTA  CAG  AAA  CAG  AGC  TGT  GAG       192
Asn  Lys  Ser  Leu  Lys  Glu  Glu  Ala  Met  Leu  Gln  Lys  Gln  Ser  Cys  Glu
     50                        55                       60

GAA  CTC  AAG  AGT  GAC  TTA  AAC  ACA  AAA  AAT  GAA  TTG  CTA  AAA  CAG  AAG       240
Glu  Leu  Lys  Ser  Asp  Leu  Asn  Thr  Lys  Asn  Glu  Leu  Leu  Lys  Gln  Lys
 65                       70                       75                       80

ACC  ATA  GAA  TTA  ACA  CGA  GCA  TGT  CAG  AAG  CAA  TAT  GAG  CTG  GAA  CAG       288
Thr  Ile  Glu  Leu  Thr  Arg  Ala  Cys  Gln  Lys  Gln  Tyr  Glu  Leu  Glu  Gln
                     85                       90                       95

GAA  TTG  GCC  TTT  TAT  AAA  ATT  GAT  GCT                                          315
Glu  Leu  Ala  Phe  Tyr  Lys  Ile  Asp  Ala
               100                      105
```

( 2 ) INFORMATION FOR SEQ ID NO:2:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

| Asp | Arg | Gln | Glu | Ala | Phe | Glu | Arg | Phe | Ser | Leu | Glu | Glu | Val | Glu | Arg |
|---|---|---|---|---|---|---|---|---|---|---|---|---|---|---|---|
| 1 | | | | 5 | | | | | 10 | | | | | 15 | |

| Leu | Glu | Arg | Asp | Leu | Glu | Lys | Lys | Met | Ile | Glu | Thr | Glu | Glu | Leu | Lys |
|---|---|---|---|---|---|---|---|---|---|---|---|---|---|---|---|
| | | | 20 | | | | | 25 | | | | | 30 | | |

| Ser | Lys | Gln | Thr | Arg | Phe | Leu | Glu | Glu | Ile | Lys | Asn | Gln | Asp | Lys | Leu |
|---|---|---|---|---|---|---|---|---|---|---|---|---|---|---|---|
| | | | 35 | | | | | 40 | | | | | 45 | | |

| Asn | Lys | Ser | Leu | Lys | Glu | Glu | Ala | Met | Leu | Gln | Lys | Gln | Ser | Cys | Glu |
|---|---|---|---|---|---|---|---|---|---|---|---|---|---|---|---|
| | 50 | | | | | 55 | | | | | 60 | | | | |

| Glu | Leu | Lys | Ser | Asp | Leu | Asn | Thr | Lys | Asn | Glu | Leu | Leu | Lys | Gln | Lys |
|---|---|---|---|---|---|---|---|---|---|---|---|---|---|---|---|
| 65 | | | | | 70 | | | | | 75 | | | | | 80 |

| Thr | Ile | Glu | Leu | Thr | Arg | Ala | Cys | Gln | Lys | Gln | Tyr | Glu | Leu | Glu | Gln |
|---|---|---|---|---|---|---|---|---|---|---|---|---|---|---|---|
| | | | | 85 | | | | | 90 | | | | | 95 | |

| Glu | Leu | Ala | Phe | Tyr | Lys | Ile | Asp | Ala |
|---|---|---|---|---|---|---|---|---|
| | | | 100 | | | | | 105 |

( 2 ) INFORMATION FOR SEQ ID NO:3:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 2...52

( x i ) SEQUENCE DESCRIPTION: SEQ ID NO:3:

| A | TCA | GAG | TAT | GCT | GAA | ATT | GAT | AAA | GCC | CCA | GAT | GAA | AGC | CCT | TAC | ATT | 49 |
|---|---|---|---|---|---|---|---|---|---|---|---|---|---|---|---|---|---|
| | Ser | Glu | Tyr | Ala | Glu | Ile | Asp | Lys | Ala | Pro | Asp | Glu | Ser | Pro | Tyr | Ile | |
| | 1 | | | | 5 | | | | | 10 | | | | | 15 | | |

| GGC | AA | | 54 |
|---|---|---|---|
| Gly | | | |

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:4:

| Ser | Glu | Tyr | Ala | Glu | Ile | Asp | Lys | Ala | Pro | Asp | Glu | Ser | Pro | Tyr | Ile |
|---|---|---|---|---|---|---|---|---|---|---|---|---|---|---|---|
| 1 | | | | 5 | | | | | 10 | | | | | 15 | |

Gly ( 2 ) INFORMATION FOR SEQ ID NO:5:

( i ) SEQUENCE CHARACTERISTICS:
        ( A ) LENGTH: 330 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence (B) LOCATION: 3...329

(xi) SEQUENCE DESCRIPTION: SEQ ID NO:5:

| GA | AAA | AAA | ATA | AGT | GCC | GCC | CCA | ACT | CGA | CTA | TCC | GAA | CTG | CCT | GAT | 47 |
|----|-----|-----|-----|-----|-----|-----|-----|-----|-----|-----|-----|-----|-----|-----|-----|-----|
|    | Lys | Lys | Ile | Ser | Ala | Ala | Pro | Thr | Arg | Leu | Ser | Glu | Leu | Pro | Asp |    |
|    | 1   |     |     |     | 5   |     |     |     |     | 10  |     |     |     |     | 15  |    |

| GAA | ATA | GAA | AAG | GCC | GAA | CCA | CCA | ATT | TTG | AGA | GCT | ACT | GAA | GAA | TTT | 95 |
|-----|-----|-----|-----|-----|-----|-----|-----|-----|-----|-----|-----|-----|-----|-----|-----|-----|
| Glu | Ile | Glu | Lys | Ala | Glu | Pro | Pro | Ile | Leu | Arg | Ala | Thr | Glu | Glu | Phe |    |
|     |     |     |     | 20  |     |     |     |     | 25  |     |     |     |     | 30  |     |    |

| AAA | CAA | CTG | GAA | GAA | GCT | ATA | CCA | CTA | AAA | AAG | ATT | TCA | GAA | GCA | GGG | 143 |
|-----|-----|-----|-----|-----|-----|-----|-----|-----|-----|-----|-----|-----|-----|-----|-----|-----|
| Lys | Gln | Leu | Glu | Glu | Ala | Ile | Pro | Leu | Lys | Lys | Ile | Ser | Glu | Ala | Gly |    |
|     |     |     | 35  |     |     |     |     | 40  |     |     |     |     | 45  |     |     |    |

| AAA | GAC | CTT | CTT | TAC | AAG | CAG | TTG | AGT | GGT | AGA | CTA | CAA | CTT | GTA | AAT | 191 |
|-----|-----|-----|-----|-----|-----|-----|-----|-----|-----|-----|-----|-----|-----|-----|-----|-----|
| Lys | Asp | Leu | Leu | Tyr | Lys | Gln | Leu | Ser | Gly | Arg | Leu | Gln | Leu | Val | Asn |    |
|     |     | 50  |     |     |     |     | 55  |     |     |     |     | 60  |     |     |     |    |

| AAA | TTA | CGC | CAG | GAA | GCT | CTG | GAT | CTA | GAA | CTG | CAG | ATG | GAA | AAG | CAA | 239 |
|-----|-----|-----|-----|-----|-----|-----|-----|-----|-----|-----|-----|-----|-----|-----|-----|-----|
| Lys | Leu | Arg | Gln | Glu | Ala | Leu | Asp | Leu | Glu | Leu | Gln | Met | Glu | Lys | Gln |    |
|     | 65  |     |     |     |     | 70  |     |     |     |     | 75  |     |     |     |     |    |

| AAG | CAG | GAA | ATT | GCC | GGA | AAG | CAG | AAG | GAG | ATT | AAG | GAC | CTG | CAA | ATA | 287 |
|-----|-----|-----|-----|-----|-----|-----|-----|-----|-----|-----|-----|-----|-----|-----|-----|-----|
| Lys | Gln | Glu | Ile | Ala | Gly | Lys | Gln | Lys | Glu | Ile | Lys | Asp | Leu | Gln | Ile |    |
| 80  |     |     |     |     | 85  |     |     |     |     | 90  |     |     |     |     | 95  |    |

| GCC | ATA | GAT | AGC | CTG | GAT | TCC | AAA | GAC | CCA | AAA | CAT | TCC | CAT | A | 330 |
|-----|-----|-----|-----|-----|-----|-----|-----|-----|-----|-----|-----|-----|-----|---|-----|
| Ala | Ile | Asp | Ser | Leu | Asp | Ser | Lys | Asp | Pro | Lys | His | Ser | His |   |     |
|     |     |     |     | 100 |     |     |     |     | 105 |     |     |     |     |   |     |

(2) INFORMATION FOR SEQ ID NO:6:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

| Lys | Lys | Ile | Ser | Ala | Ala | Pro | Thr | Arg | Leu | Ser | Glu | Leu | Pro | Asp | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Glu | Lys | Ala | Glu | Pro | Pro | Ile | Leu | Arg | Ala | Thr | Glu | Glu | Phe | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Leu | Glu | Glu | Ala | Ile | Pro | Leu | Lys | Lys | Ile | Ser | Glu | Ala | Gly | Lys |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Leu | Leu | Tyr | Lys | Gln | Leu | Ser | Gly | Arg | Leu | Gln | Leu | Val | Asn | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Leu | Arg | Gln | Glu | Ala | Leu | Asp | Leu | Glu | Leu | Gln | Met | Glu | Lys | Gln | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Glu | Ile | Ala | Gly | Lys | Gln | Lys | Glu | Ile | Lys | Asp | Leu | Gln | Ile | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ile | Asp | Ser | Leu | Asp | Ser | Lys | Asp | Pro | Lys | His | Ser | His |
|-----|-----|-----|-----|-----|-----|-----|-----|-----|-----|-----|-----|-----|
|     |     |     | 100 |     |     |     |     | 105 |     |     |     |     |

(2) INFORMATION FOR SEQ ID NO:7:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: cDNA (ix) FEATURE:

( A ) NAME/KEY: Coding Sequence
        ( B ) LOCATION: 1...144

( x i ) SEQUENCE DESCRIPTION: SEQ ID NO:7:

```
AAG  AGC  GGT  AAA  GAA  CAA  CAG  CTT  GAC  ATT  ATG  AAC  AAG  CAG  TAC  CAA         48
Lys  Ser  Gly  Lys  Glu  Gln  Gln  Leu  Asp  Ile  Met  Asn  Lys  Gln  Tyr  Gln
 1              5                        10                       15

CAA  CTT  GAA  AGT  CGT  TTG  GAT  GAG  ATA  CTT  TCT  AGA  ATT  GCT  AAG  GAA         96
Gln  Leu  Glu  Ser  Arg  Leu  Asp  Glu  Ile  Leu  Ser  Arg  Ile  Ala  Lys  Glu
               20                       25                       30

ACG  GAA  GAG  ATT  AAG  GAC  CTT  GAA  GAA  CAG  CTT  ACT  GAA  GGC  CAG  ATA  G     145
Thr  Glu  Glu  Ile  Lys  Asp  Leu  Glu  Glu  Gln  Leu  Thr  Glu  Gly  Gln  Ile
          35                       40                       45

C                                                                                      146
```

( 2 ) INFORMATION FOR SEQ ID NO:8:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:8:

```
Lys  Ser  Gly  Lys  Glu  Gln  Gln  Leu  Asp  Ile  Met  Asn  Lys  Gln  Tyr  Gln
 1              5                        10                       15

Gln  Leu  Glu  Ser  Arg  Leu  Asp  Glu  Ile  Leu  Ser  Arg  Ile  Ala  Lys  Glu
               20                       25                       30

Thr  Glu  Glu  Ile  Lys  Asp  Leu  Glu  Glu  Gln  Leu  Thr  Glu  Gly  Gln  Ile
          35                       40                       45
```

( 2 ) INFORMATION FOR SEQ ID NO:9:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 2...112

( x i ) SEQUENCE DESCRIPTION: SEQ ID NO:9:

```
A  AAT  GAA  GCC  CTG  AAG  AAG  GAT  TTA  GAA  GGT  GTT  ATC  AGT  GGG  TTG  CAA      49
   Asn  Glu  Ala  Leu  Lys  Lys  Asp  Leu  Glu  Gly  Val  Ile  Ser  Gly  Leu  Gln
    1              5                        10                       15

GAA  TAC  CTG  GGG  ACC  ATT  AAA  GGC  CAG  GCA  ACT  CAG  GCC  CAG  AAT  GAG         97
Glu  Tyr  Leu  Gly  Thr  Ile  Lys  Gly  Gln  Ala  Thr  Gln  Ala  Gln  Asn  Glu
               20                       25                       30

TGC  AGG  AAG  CTG  CGG  G                                                             113
Cys  Arg  Lys  Leu  Arg
          35
```

( 2 ) INFORMATION FOR SEQ ID NO:10:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:10:

```
Asn  Glu  Ala  Leu  Lys  Lys  Asp  Leu  Glu  Gly  Val  Ile  Ser  Gly  Leu  Gln
 1              5                        10                       15

Glu  Tyr  Leu  Gly  Thr  Ile  Lys  Gly  Gln  Ala  Thr  Gln  Ala  Gln  Asn  Glu
               20                        25                       30

Cys  Arg  Lys  Leu  Arg
          35
```

( 2 ) INFORMATION FOR SEQ ID NO:11:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 2...373

( x i ) SEQUENCE DESCRIPTION: SEQ ID NO:11:

```
A  AGT  GCC  CTC  CAA  GAG  CAG  CAT  GAG  GTG  AAT  GCA  TCT  TTG  CAG  CAG  ACC    49
   Ser  Ala  Leu  Gln  Glu  Gln  His  Glu  Val  Asn  Ala  Ser  Leu  Gln  Gln  Thr
    1              5                        10                       15

CAG  GGA  GAT  CTC  AGT  GCC  TAT  GAA  GCT  GAG  CTA  GAG  GCT  CGG  CTA  AAC       97
Gln  Gly  Asp  Leu  Ser  Ala  Tyr  Glu  Ala  Glu  Leu  Glu  Ala  Arg  Leu  Asn
               20                        25                       30

CTA  AGG  GAT  GCT  GAA  GCC  AAC  CAG  CTC  AAG  GAA  AAG  TTG  GAA  AAA  GTA      145
Leu  Arg  Asp  Ala  Glu  Ala  Asn  Gln  Leu  Lys  Glu  Lys  Leu  Glu  Lys  Val
          35                        40                        45

ACA  AGA  CTT  ACC  CAG  TTA  GAA  CAA  TCA  GCC  CTT  CAA  GCA  GAA  CTT  GAG      193
Thr  Arg  Leu  Thr  Gln  Leu  Glu  Gln  Ser  Ala  Leu  Gln  Ala  Glu  Leu  Glu
     50                        55                        60

AAG  GAA  AGG  CAA  GCC  CTC  AAG  AAT  GCC  CTT  GGA  AAA  GCC  CAG  TTC  TCA      241
Lys  Glu  Arg  Gln  Ala  Leu  Lys  Asn  Ala  Leu  Gly  Lys  Ala  Gln  Phe  Ser
65                       70                        75                        80

GAA  GAA  AAG  GAG  CAA  GAG  AAC  AGT  GAG  CTC  CAT  GCA  AAA  CTT  AAA  CAC      289
Glu  Glu  Lys  Glu  Gln  Glu  Asn  Ser  Glu  Leu  His  Ala  Lys  Leu  Lys  His
                    85                        90                       95

TTG  CAG  GAT  GAC  AAT  AAT  CTG  TTA  AAA  CAG  CAA  CTT  AAA  GAT  TTC  CAG      337
Leu  Gln  Asp  Asp  Asn  Asn  Leu  Leu  Lys  Gln  Gln  Leu  Lys  Asp  Phe  Gln
               100                       105                      110

AAT  CAC  CTT  AAC  CAT  GTG  GTT  GAT  GGT  TTG  GTT  CGT  CC                      375
Asn  His  Leu  Asn  His  Val  Val  Asp  Gly  Leu  Val  Arg
          115                       120
```

( 2 ) INFORMATION FOR SEQ ID NO:12:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:12:

| Ser | Ala | Leu | Gln | Glu | Gln | His | Glu | Val | Asn | Ala | Ser | Leu | Gln | Gln | Thr |
| 1 | | | | 5 | | | | | 10 | | | | | 15 | |

| Gln | Gly | Asp | Leu | Ser | Ala | Tyr | Glu | Ala | Glu | Leu | Glu | Ala | Arg | Leu | Asn |
| | | | 20 | | | | | 25 | | | | | 30 | | |

| Leu | Arg | Asp | Ala | Glu | Ala | Asn | Gln | Leu | Lys | Glu | Lys | Leu | Glu | Lys | Val |
| | | 35 | | | | | 40 | | | | | 45 | | | |

| Thr | Arg | Leu | Thr | Gln | Leu | Glu | Gln | Ser | Ala | Leu | Gln | Ala | Glu | Leu | Glu |
| | 50 | | | | | 55 | | | | | 60 | | | | |

| Lys | Glu | Arg | Gln | Ala | Leu | Lys | Asn | Ala | Leu | Gly | Lys | Ala | Gln | Phe | Ser |
| 65 | | | | | 70 | | | | | 75 | | | | | 80 |

| Glu | Glu | Lys | Glu | Gln | Glu | Asn | Ser | Glu | Leu | His | Ala | Lys | Leu | Lys | His |
| | | | | 85 | | | | | 90 | | | | | 95 | |

| Leu | Gln | Asp | Asp | Asn | Asn | Leu | Leu | Lys | Gln | Gln | Leu | Lys | Asp | Phe | Gln |
| | | | 100 | | | | | 105 | | | | | 110 | | |

| Asn | His | Leu | Asn | His | Val | Val | Asp | Gly | Leu | Val | Arg |
| | | 115 | | | | | 120 | | | | |

( 2 ) INFORMATION FOR SEQ ID NO:13:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 1...228

( x i ) SEQUENCE DESCRIPTION: SEQ ID NO:13:

| AAA | CTG | AAA | TTA | GGA | ACT | GGG | GAA | ATG | AAC | ATC | CAT | AGT | CCT | TCA | GAT | 48 |
| Lys | Leu | Lys | Leu | Gly | Thr | Gly | Glu | Met | Asn | Ile | His | Ser | Pro | Ser | Asp | |
| 1 | | | | 5 | | | | | 10 | | | | | 15 | | |

| GTC | TTA | GGG | AAA | AGT | CTT | GCT | GAT | TTA | CAG | AAA | CAA | TTC | AGT | GAA | ATT | 96 |
| Val | Leu | Gly | Lys | Ser | Leu | Ala | Asp | Leu | Gln | Lys | Gln | Phe | Ser | Glu | Ile | |
| | | | 20 | | | | | 25 | | | | | 30 | | | |

| CTT | GCA | CGC | TCC | AAG | TGG | GAA | AGA | GAT | GAA | GCA | CAA | GTT | AGA | GAG | AGA | 144 |
| Leu | Ala | Arg | Ser | Lys | Trp | Glu | Arg | Asp | Glu | Ala | Gln | Val | Arg | Glu | Arg | |
| | | 35 | | | | | 40 | | | | | 45 | | | | |

| AAA | CTC | CAA | GAA | GAA | ATG | GCT | CTG | CAG | CAA | GAG | AAA | CTG | GCA | ACT | GGA | 192 |
| Lys | Leu | Gln | Glu | Glu | Met | Ala | Leu | Gln | Gln | Glu | Lys | Leu | Ala | Thr | Gly | |
| | 50 | | | | | 55 | | | | | 60 | | | | | |

| CAA | GAA | GAG | TTC | AGG | CAG | GCC | TGT | GAG | AGA | GCC | CTG | | | | | 228 |
| Gln | Glu | Glu | Phe | Arg | Gln | Ala | Cys | Glu | Arg | Ala | Leu | | | | | |
| 65 | | | | 70 | | | | | 75 | | | | | | | |

( 2 ) INFORMATION FOR SEQ ID NO:14:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:14:

| Lys | Leu | Lys | Leu | Gly | Thr | Gly | Glu | Met | Asn | Ile | His | Ser | Pro | Ser | Asp |
| 1 | | | | 5 | | | | | 10 | | | | | 15 | |

| Val | Leu | Gly | Lys | Ser | Leu | Ala | Asp | Leu | Gln | Lys | Gln | Phe | Ser | Glu | Ile |

|Leu|Ala|Arg|Ser|Lys|Trp|Glu|Arg|Asp|Glu|Ala|Gln|Val|Arg|Glu|Arg|
| | |35| | | | |40| | | | |45| | | |

|Lys|Leu|Gln|Glu|Glu|Met|Ala|Leu|Gln|Gln|Glu|Lys|Leu|Ala|Thr|Gly|
| |50| | | | |55| | | | |60| | | | |

|Gln|Glu|Glu|Phe|Arg|Gln|Ala|Cys|Glu|Arg|Ala|Leu|
|65| | | | |70| | | |75| | |

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:15:

CGAGCATGTC AGAAGCAATA TG      22

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:16:

CCCAGATGAA AGCCCTTAC      19

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:17:

AGCCCTTACA TTGGCAAATC      20

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:18:

CAGGCAGTAC AGATCAAGAA G      21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:19:

GAACTTGAGA GGCCACACAC 20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:20:

TAAATTACGC CAGGAACGTC 20

( 2 ) INFORMATION FOR SEQ ID NO:21:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:21:

GCCAGATAGC AGCAAAATGA AG 22

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:22:

TACTGGCTGA CCTTCCAAAC 20

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:23:

AGCCTCCTGT CTATCCTGAG TG 22

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:24:

GTCTCTTTCC AGTCTTTCTA CCTC 24

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:25:

CTTCTTAGCT CATCCACAC       19

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:26:

GAACCAAACC ATCAACCAC       19

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:27:

GAAGGGCTGA TTGTTCTAAC TG       22

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:28:

TTCTAGCTCT GCAAGCTCCT C       21

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide primer (xi) SEQUENCE DESCRIPTION: SEQ ID NO:29:

ACTTTCTAGC TCTGCAAGCT CC       22

(2) INFORMATION FOR SEQ ID NO:30:

(i) SEQUENCE CHARACTERISTICS:

( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:30:

CAACCCACTG ATAACACCTT C 21

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:31:

GTCAAGCTGT TGTTCTTTAC CG 22

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:32:

GGACAAGAAG AGTTCAGGCA G 21

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:33:

ACTGGACAAG AAGAGTTCAG G 21

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide primer ( x i ) SEQUENCE DESCRIPTION: SEQ ID NO:34:

ACTCCAAGAA GAAATGGCTC 20

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear -continued (ii) MOLECULE TYPE: oligonucleotide primer (xi) SEQUENCE DESCRIPTION: SEQ ID NO:35:

GAGGTAGAAA GACTGGAAAG AGAC                         24

(2) INFORMATION FOR SEQ ID NO:36:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: oligonucleotide primer (xi) SEQUENCE DESCRIPTION: SEQ ID NO:36:

TGCCTGAACT CTTCTTGTCC                              20

DIAGNOSTIC METHODS FOR SCREENING PATIENTS FOR SCLERODERMA

BACKGROUND OF THE INVENTION

The invention relates to cell biology, autoimmune disorders, and diagnosis of scleroderma.

Scleroderma, or systemic sclerosis, is characterized by deposition of fibrous connective tissue in the skin, and often in many other organ systems. It may be accompanied by vascular lesions, especially in the skin, lungs, and kidneys. The course of this disease is variable, but it is usually slowly progressive. Scleroderma may be limited in scope and compatible with a normal life span. Systemic involvement, however, can be fatal.

Scleroderma is classified as diffuse or limited, on the basis of the extent of skin and internal organ involvement. The diffuse form is characterized by thickening and fibrosis of skin over the proximal extremities and trunk. The heart, lungs, kidneys, and gastrointestinal tract below the esophagus are often involved. Limited scleroderma is characterized by cutaneous involvement of the hands and face. Visceral involvement occurs less commonly. The limited form has a better prognosis than the diffuse form, except when pulmonary hypertension is present.

Antinuclear antibodies are found in over 95 percent of patients with scleroderma. Specific antinuclear antibodies have been shown to be directed to topoisomerase I, centromere proteins, RNA polymerases, or nucleolar components. Different antibodies are associated with particular clinical patterns of scleroderma. For example, antibodies to topoisomerase I (Scl-70) and to RNA polymerases (usually RNA polymerase III) are seen in patients with diffuse scleroderma. Antibodies to nuclear ribonucleoprotein (nRNP) are associated with diffuse and limited scleroderma. Certain anticentromere antibodies are associated with limited scleroderma or the CREST syndrome; however, the particular centromere antigen or antigens have not been identified.

Patients with scleroderma show autoreactivity against centrosomes (Tuffanelli, et al., Arch. Dermatol., 119:560–566, 1983). Centrosomes are essential structures that are highly conserved, from plants to mammals, and are important for various cellular processes. Centrosomes play a crucial role in cell division and its regulation. Centrosomes organize the mitotic spindle for separating chromosomes during cell division, thus ensuring genetic fidelity. In most cells, the centrosome includes a pair of centrioles that lie at the center of a dense, partially filamentous matrix, the pericentriolar material (PCM). The microtubule cytoskeleton is anchored to the centrosome or some other form of microtubule organizing center (MTOC), which is thought to serve as a site of microtubule nucleation.

Little is known about how centrosomes perform their cellular functions or the molecular components that are involved. A limited number of proteins and antigens associated with centrosomes have been described. For reviews, see Kuriyama, "Monoclonal Antibodies to MTOC-antigens," The Centrosome, p. 131–165 (Kalnins (ed.) Academic Press, Inc. San Diego 1992); Kalt et al., Trends in Cell Biol., 3:118–128, 1993).

SUMMARY OF THE INVENTION

In general, the invention features diagnostic methods for testing biological samples for evidence of the disease scleroderma. The methods use a fragment of a highly conserved centrosomal protein designated CP140, an isolated DNA encoding the CP140 fragment, oligonucleotide PCR primers based on the isolated DNA encoding the CP140 fragment, or a purified CP140-specific antibody.

The invention includes a diagnostic method for screening a patient for the presence of anti-CP140 autoantibodies as an indication of sclerotic disease. The method includes the steps of: (a) obtaining a biological sample from the patient; (b) obtaining a substantially pure CP140 polypeptide fragment; (c) contacting the sample with the CP140 polypeptide fragment under conditions that allow the CP140 fragment to bind to anti-CP140 autoantibodies; and (d) detecting anti-CP140 autoantibody:CP140 complexes as an indication of the presence of sclerotic disease in the patient. Methods for contacting the sample with the CP140 polypeptide fragment and detecting autoantibody:CP140 complexes include Western blot analysis and ELISA. The CP140 polypeptide fragment can comprise one or more of the following amino acid sequences: SEQ ID NO:2, SEQ ID NO:4, SEQ ID NO:6, SEQ ID NO:8, SEQ ID NO:10, SEQ ID NO:12, or SEQ ID NO:14. The substantially pure CP140 polypeptide fragment can be part of a fusion protein. In one embodiment, a CP140 fragment fusion protein includes a glutathione-S-transferase (GST) carrier moiety.

The invention also includes another method for screening a patient for the presence of anti-CP140 autoantibodies as an indication of sclerotic disease. The method includes the steps of: (a) obtaining a culture of non-sclerotic human cells that contain CP140; (b) permeabilizing the non-sclerotic human cells to allow entry of antibodies into the cells; (c) obtaining a biological sample from the patient; (d) contacting the sample with the permeabilized cells; (e) adding a purified CP140-specific antibody to the permeabilized cells; and (f) detecting cells that contain co-localized anti-CP140 autoantibody:CP140 complexes and purified anti-CP140 antibody:CP140 complexes. The purified anti-CP140 antibody can bind to a CP140 polypeptide fragment comprising one or more of the following sequences: SEQ ID NO:2, SEQ ID NO:4, SEQ ID NO:6, SEQ ID NO:8, SEQ ID NO:10, SEQ ID NO:12, and SEQ ID NO:14.

The invention also includes a method for screening a patient for a altered CP140 mRNA level as an indication of sclerotic disease. The method includes the steps of: (a) obtaining a patient cell sample; (b) isolating total mRNA from the cell sample; (c) obtaining total cDNA from the total MRNA; (d) amplifying a CP140 cDNA fragment from the total cDNA; and (e) detecting a change in the quantity of amplified CP140 cDNA fragment in the cell sample compared to the quantity of amplified CP140 cDNA fragment from a sample of non-sclerotic cells. The amplifying step can be performed with a polymerase chain reaction.

In addition, the invention includes a method for ascreening a patient for altered CP140 protein level as an indication of sclerotic disease. The method includes the steps of: (a) obtaining a sample of cells from a patient; and (b) detecting a change in a quantity of CP140 protein in the cells compared to the quantity of CP140 protein in a sample of non-sclerotic cells.

The invention also includes a method for screening a patient for an alteration in the CP140 gene as an indication of sclerotic disease. The method includes the steps of: (a) obtaining a sample of patient cells and a control sample of non-sclerotic cells; (b) isolating total DNA from the cells in the patient sample and the control sample; (c) selectively amplifying CP140 DNA from the total DNA of the patient sample and the control sample; and (d) comparing the amplified patient CPl40 DNA and the amplified control CP140 DNA. A variation in the DNA from the patient cells compared to the DNA from the control cells indicates the presence of sclerotic disease in the patient. The amplified CP140 DNA from the patient sample and the control sample can be digested with restriction enzymes to create DNA fragments that are compared. The selective amplifying step can be performed with a polymerase chain reaction.

The invention also includes an isolated DNA that includes a nucleotide sequence resulting from a polymerase chain reaction using a 5' primer consisting of GAGGTAGAAA GACTGGAAAG AGAC (SEQ ID NO:35), a 3' primer consisting of TGCCTGAACT CTTCTTGTCC (SEQ ID NO:36), and DNA template material from non-sclerotic human cells. The invention also includes an isolated DNA that includes a nucleotide sequence that encodes a CP140 epitope and defines a DNA that hybridizes under stringent hybridization conditions to above-described DNA. The invention also includes a vector comprising the isolated DNA. Preferably, the DNA is operatively linked to an expression control sequence. The invention also includes a cell containing the isolated DNA.

The invention also includes a method of making a substantially pure CPl40 fragment fusion protein. The method includes the steps of: (a) obtaining a DNA that includes a nucleotide sequence resulting from a polymerase chain reaction using a 5' primer consisting of GAGGTAGAAA GACTGGAAAG AGAC (SEQ ID NO:35), a 3' primer consisting of TGCCTGAACT CTTCTTGTCC (SEQ ID NO:36), and DNA template material from non-sclerotic human cells; (b) inserting the DNA into an expression vector so that the nucleotide sequence encoding CP140 fragment is ligated in the same reading frame with, and directly adjacent to, a nucleotide sequence encoding at least a portion of a non-human protein, thereby producing a heterologous gene construct encoding a CP140 fragment fusion protein; (c) transforming a host cell with the expression vector; (d) culturing the host cell so as to allow expression of the heterologous gene construct; and (e) collecting the CP140 fragment fusion protein. The invention also includes a CP140 fragment fusion protein made by this process. The invention also includes a substantially pure free CP140 polypeptide fragment, i.e., without a fused carrier protein moiety. The invention also includes a substantially pure CP140-specific antibody.

As used herein, "antibody" means monoclonal or polyclonal antibodies, whole, intact antibodies or antibody fragments having the immunological activity of the whole antibody.

As used herein, "autoantibody" means an antibody that reacts with an antigenic constituent of normal cells or normal tissues of the organism producing the antibody.

As used herein, "CP140-specific" antibody means an antibody that binds to a CP140 polypeptide or fragment thereof and does not bind to other human proteins. The term includes polyclonal and monoclonal antibodies.

As used herein "polypeptide" means any peptide-linked chain of amino acids, regardless of length or post-translational modification (e.g., glycosylation or phosphorylation).

As used herein, "isolated DNA" means DNA free of the genes that flank the gene of interest in the genome of the organism in which the gene of interest naturally occurs. The term therefore includes a recombinant DNA that is incorporated into a vector, into an autonomously replicating plasmid or virus, or into the genomic DNA of a prokaryote or eukaryote. It also includes a separate molecule such as a cDNA, a genomic DNA, a fragment produced by PCR, or a restriction fragment. The term also includes a recombinant nucleotide sequence that is part of a hybrid gene, i.e., a gene encoding a fusion protein.

As used herein, "stringent hybridization conditions" means the following conditions: hybridization at 42° C. in the presence of 50% formamide; a first wash at 65° C. with 2×SSC containing 1% SDS; followed by a second wash at 65° C. with 0.1×SSC.

As used herein, "substantially pure" polypeptide means a polypeptide separated from components that naturally accompany it. Typically, the polypeptide is substantially pure when is at least 60%, by weight, free from the proteins and naturally-occurring organic molecules with which it is naturally associated. Preferably, the purity of the preparation is at least 75%, more preferably at least 90%, and most preferably at least 99%, by weight. A substantially pure CP140 polypeptide fragment can be obtained, for example, by extraction from a natural source, by expression of a recombinant nucleic acid encoding a CP140 polypeptide fragment, by expression of a CP140 polypeptide fragment fusion protein, or by chemical synthesis. A chemically synthesized polypeptide or a polypeptide produced in a cellular system different from the cell from which it naturally occurs is, by definition, substantially free from components that naturally accompany it. Accordingly, substantially pure polypeptides include those derived from eukaryotic organisms but synthesized in recombinant cells of E. coli or other prokaryotes. Purity can be measured by any appropriate methods, e.g., column chromatography, polyacrylamide gel electrophoresis, or by HPLC analysis.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

BRIEF DESCRIPTION OF THE DRAWINGS

FIG. 1A–1E is a chart containing nucleotide sequences from a CP140 partial cDNA. FIG. 1A–1E also shows amino acid sequences deduced from the nucleotide sequences.

FIG. 3 is a table listing oligonucleotide primer sequences based on nucleotide sequences from a CP140 cDNA.

DETAILED DESCRIPTION

Figure 1E:
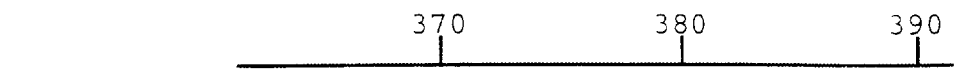

Autoantibody-containing antisera from three different scleroderma patients were used to identify a CDNA clone expressing part of a novel centrosomal protein called CP140. A partial nucleotide sequence contains an opep reading frame of 1.7 kb (FIG. 1A–1E). The antisera recognized a 140 kd protein and stained centrosomes.

CP140 is a highly conserved, coiled-coil protein present in all centrosomes so far tested. It is exclusively localized to centrosomes, as shown by its association with centrosomes isolated from cultured cells. CP140 levels change with the nucleating capacity of centrosomes during the cell cycle. The function of CP140 was tested by injecting anti-CP140 antibodies into Xenopus embryos, where they blocked mitotic cell division.

Isolation of a cDNA Encoding CP140

An autoimmune serum from a patient with scleroderma, designated 5051, has been used as an immunofluorescence marker for centrosomes and other microtubule organizing centers, Tuffanelli, et al., *Arch. Dermatol.,* 119:560–566 (1983); Calarco et al.,*J. Cell Biol.,* 101:319–324 (1983); and Clayton et al., *Cell,* 35:621–629 (1985). The antigen(s) recognized by the serum is conserved, from plants to humans. To identify genes encoding the 5051 antigen, a human placental λgtII cDNA expression library was screened with 5051 and two autoimmune sera from individual scleroderma patients. Procedures were essentially as described by Sambrook et al., *Molecular Cloning: A Laboratory Manual* (Cold Spring Harbor, N.Y., Cold Spring Harbor Laboratory Press, 1989).

The cloning of CP140 was difficult for several reasons. Cloning was complicated because the human autoimmune sera used to identify CP140 had low affinity for CP140 and gave high background on Western blots. The sera also gave high backgrounds in the screening of lambda gt11 expression libraries. To overcome this background, a variety of blocking agents (milk, BSA, serum from horse, and goat, and lysate from bacteria) were used in library screening as described below. Even with combinations of these blocking agents, the CP140 signal was only 2- to 3-fold higher than background.

A further difficulty was that a large amount of autoimmune serum was required for the extensive screening required to initially detect CP140. That was because the CP140 mRNAs was present in very low abundance. It was necessary to screen about 50 million plaques in four different libraries to obtain a CP140 CDNA. Autoimmune sera were diluted 1:500 in PBS and 5% BSA. They were then incubated with filters, together with bacterial lysate to reduce background. Out of $5\times10^7$ plaques screened, only one 1.7 kb cDNA was identified (designated λpc1.1). The CP140 partial cDNA was subcloned into a Bluescript vector (Stratagene, LaJolla, Calif.).

The partial cDNA was subjected to sequence analysis, using the dideoxy chain termination method. Sequence analysis revealed that the CP140 partial cDNA contained one continuous open reading frame. FIGS. 1A–1E shows partial nucleotide sequences (SEQ ID NO:1, SEQ ID NO:3, SEQ ID NO:5, SEQ ID NO:7, SEQ ID NO:9, SEQ ID NO:11, and SEQ ID NO:13) from the CP140 partial cDNA clone, and the deduced amino acid sequences (SEQ ID NO:2, SEQ ID NO:4, SEQ ID NO:6, SEQ ID NO:8, SEQ ID NO:10, SEQ ID NO:12, and SEQ ID NO:14) encoded by the nucleotide sequences.

Fusion Protein Production

The original CP140 CDNA of 1.7kb was subcloned into *E. coli* expression vector pGEX-1 (Amrad Corp., Australia). The resulting fusion protein was overexpressed in *E. coli*. The fusion protein consisted of approximately 70 kd of CP140 and 26kd of glutathione-S-transferase (GST) (Smith et al., *Gene* 67:31–40, 1988).

The GST::CP140 fusion protein was purified using commercially-available GST columns according to the vendor's recommendations (Amrad Corp., Abbots Ford, Victoria, Australia). Unfused GST proteins were also produced, purified, and used for control purposes.

A CP140 fragment can be expressed as part of a fusion protein wherein a specific proteolytic cleavage site is placed immediately adjacent to the CP140 amino acid sequence. When, the free CP140 polypeptide fragment can be obtained in purified form, by conventional techniques. For example, the CP140 cDNA can be cloned into plasmid pGEX-2T (Smith et al., supra). Insertion of a CP140 cDNA between the SmaI and EcoRI sites of pGEX-2T will result in the expression of a GST::CP140 fusion protein that can be purified on a glutathione-agarose affinity column. Cleavage of the purified fusion protein with thrombin generates two fragments, a GST carrier fragment and a CP140 fragment. Thrombin does not cleave the GST carrier fragment. After proteolysis, the GST carrier fragment and uncleaved fusion protein can be removed by adsorption on a glutathione-agarose column, leaving the purified CP140 fragment.

Antibodies

The GST::CP140 fusion protein (100 kd) was gel purified, electroeluted, and used to raise antisera in rabbits using standard techniques (Babco Inc., Emeryville, Calif.). Antibodies were affinity-purified using fusion proteins and unfused vector proteins (GST) essentially as described by Harlow and Lane, *Antibodies: A Laboratory Manual* (Cold Spring Harbor, New York: Cold Spring Harbor Laboratory Press, 1988). Anti-CP140 antiserum was passed directly over a column of GST::CP140 fusion protein. Affinity-purified antibody fractions contained 95% IgG and reacted with centrosomes by immunofluorescence and with the fusion protein on Western blots.

Several controls were used, including affinity-purified anti-GST antibodies, an IgG fraction purified from the preimmune serum using protein A beads (Sigma Chem. Corp., St. Louis, Mo.) and eluted under the same conditions used for anti-CP140 antibodies, and a rabbit IgG fraction (Sigma, St. Louis, Mo.). In all experiments, anti-CP140 and control antibodies were concentrated to 2 mg/ml and dialyzed against the appropriate buffer.

Monoclonal antibodies can also be made with the purified human CP140 polypeptide or fusion protein using standard hybridoma technology (see, e.g., Kohler et al., *Nature,* 256:495, 1975; Kohler et al., *Eur. J. Immunol.,* 6:511, 1976; Kohler et al., *Eur. J. Immunol.,* 6:292, 1976; Hammerling et al., *Monoclonal Antibodies and T Cell Hybridomas,* Elsevier, N.Y., 1981; and Ausubel et al., *Current Protocols in Molecular Biology,* John Wiley & Sons, New York, 1994).

Once produced, polyclonal or monoclonal antibodies are tested for CP140 binding specificity. This can be done, for example, by Western blot or immunoprecipitation analysis (Ausubel et al., supra). Antibodies that specifically recognize a CP140 protein or a portion thereof, are used, e.g., for diagnostic screening.

CP140 is a 140 kd Centrosome Protein

Western blots demonstrated that the anti-CP140 antibodies and the original 5051 antisera both recognized the lookd GST::CP140 fusion protein. Affinity-purified anti-CP140 antibodies, but not pericentrin sera or anti-tubulin antibody (DM1a, Sigma), recognized a protein of ≈140 kd in cellular fractions enriched in centrosomes. CP140 was not detectable in whole cell lysates. This suggested that the protein was rare.

CP140 Predicted to be Large Coiled-Coil Protein with Non-Coiled Ends

The partial polypeptide sequence of CP140 was compared to known translated sequences in several databases. The entire length of the CP140 clone was weakly homologous to coiled-coil domains of several other proteins such as myosin and keratin.

Further analysis according to the method of Lupas et al. (*Science*, 252:1162–1164 (1991)) indicated that CP140 was long α-helical, coiled-coil protein. Several coiled-coil segments are found in the α-helical domain of CP140, interrupted by short segments that lack heptad periodicity and are similar to those found in some other coiled-coil proteins such as laminin. These segments often contain proline residues, which usually disrupt α-helices.

Though coiled domains of other coiled-coil proteins are often involved in interactions with other proteins, no consensus sequences for microtubule binding, or nucleotide binding, e.g., as seen in motor proteins, were found.

Testing of Anti-CP140 Antibodies

Antibodies raised against the original fusion protein were tested for their ability to stain centrosomes by immunofluorescence. Cultured cells and isolated centrosomes were processed for immunofluorescence as described previously in Mitchison et al., *Nature*, 312:232–237 (1984), using MeOH (−20° C.) as the fixative. Affinity-purified anti-CP140 antibody was used at 5 µg/ml, and all other sera at 1:500.

In Cos cells, the fusion protein antibodies gave the characteristic centrosome staining pattern of one or two foci in the perinuclear region of interphase cells. No staining was seen with pre-immune serum.

The species specificity of anti-CP140 antibodies was tested. The original antibody recognized centrosomes in human, mouse, and frog cells. The strong centrosome staining in mammals and amphibians demonstrated CP140 to be a highly conserved protein.

CP140 appears to be an integral component of the centrosome and not simply material that is transported there along microtubules. Complete depolymerization of microtubules did not change the staining pattern of CP140 observed in untreated cells. Similar results were obtained with cytochalasin, which depolymerizes actin filaments. When both drugs were used to isolate centrosomes from cultured Chinese hamster ovary (CHO) or HeLa cells, CP140 staining co-localized with the anti-α-tubulin and anti-CP140 antibodies. Treatment of cells with nonionic detergents did not alter the staining pattern. Thus, CP140 is a robust and integral part of the centrosome.

In Vivo Assays of CP140 Function

Anti-CP140 antibodies inhibited cell division in Xenopus embryos. Xenopus eggs and embryos were injected with 25–50 nl of antibody solution (0.2–2.0 mg/ml) at the two cell stage as described in Amaya et al., *Cell*, 66:257–270 (1991). For immunofluorescence studies, thinner needles were used to inject all cells of 4- to 8-cell embryos with appropriate (5–10 nl) volumes. Eggs and embryos were incubated for 2.5–3 hours at room temperature before processing. A total of 438 cells from anti-CP140-injected embryos and 302 cells from control antibody-injected embryos were analyzed in four experiments using two anti-CP140 antibody preparations.

The antibodies, which react with the native Xenopus protein, were injected into one cell of a two-cell embryo. Uninjected cells divided normally, while cells injected with anti-CP140 antibodies divided 1–5 times and then arrested.

Incidence of Centrosome Reactivity in Patients with Scleroderma

The incidence of centrosome reactivity in scleroderma is higher than all other autoantigens. It is believed that the reported incidence of centrosome autoreactivity in patients with scleroderma (7%) has been underestimated, prior to the present invention. It is difficult to detect centrosome staining by immunofluorescence—the only method for screening sera for centrosome reactivity until now—because the centrosome is a single tiny fluorescent dot not easily detected by conventional methods. The centrosome is usually located near the nucleus and at the convergence of microtubules. Many autoimmune sera have either prevalent nuclear staining or high background staining of the cytoplasm which obscures the centrosome staining. Finally, fixation procedures are often incompatible with antibody reactivity. This is another factor contributing to underestimation of centrosome autoreactivity in scleroderma.

To increase the sensitivity of centrosome detection, we developed a biochemical assay based on the ability of autoimmune sera to react with recombinant centrosome proteins. Bacterially-expressed, pericentrin and CP140 were partially purified, separated from other proteins by SDS-gel electrophoresis and tested for autoantibody reactivity by Western blotting with auto-immune sera from scleroderma patients at dilutions optimized for reactivity with other scleroderma autoantigens ($10^{-3}$). In this assay, positive sera gave strong signals comparable to positive controls.

Figure 2:
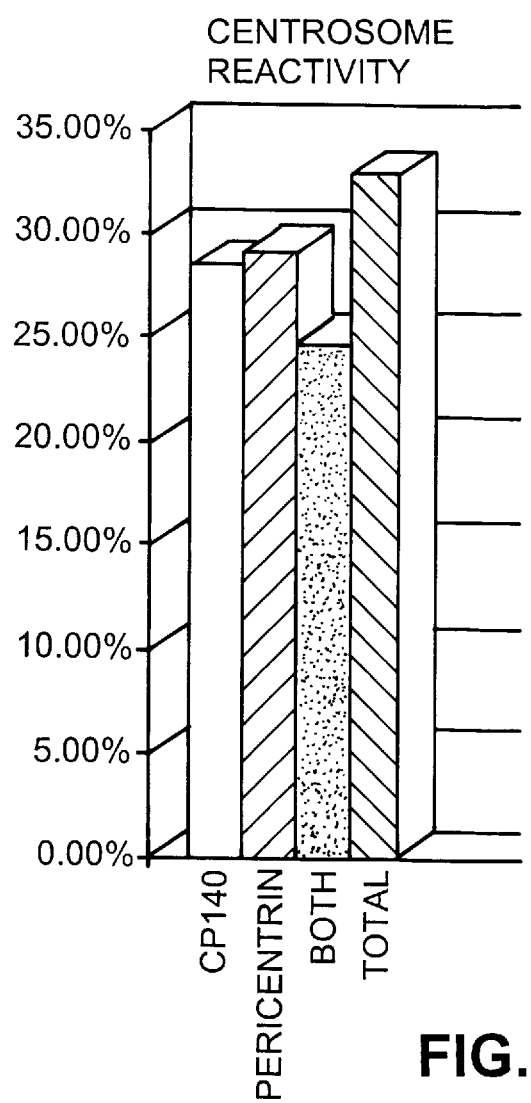
FIG. 2 is a bar graph showing reactivity of scleroderma patient sera (expressed as percent of total) against CP140 and pericentrin.

Using this assay, we have analyzed 137 scleroderma sera. The results are summarized in FIG. 2. We found that 28.5% react with CP140, 29.1% react with pericentrin, 24.5% react with both centrosome autoantigens and that the total centrosome reactivity to both antigens is 32.9%. We tested pooled sera from 30 normal control patients, and found no autoimmune reactivity against CP140. These results indicate that the prevalence of centrosome reactivity in scleroderma sera is significantly higher (about 33%) than previously believed. In fact, it is more prevalent than any other scleroderma autoantigen described to date. It was observed that 40% of all seropositive patients were negative for antitopoisomerase-1 and anticentromere reactivity. This indicates that anticentrosome autoreactivity represents a novel and significant category of scleroderma reactivity.

Use

The autoreactivity to CP140 of 28% of scleroderma patient sera tested (38 out of 137) indicates that anti-CP140 autoantibodies in the sera of these patients serve as a diagnostic marker for the disease. Alterations in the CP140 gene or in gene or protein expression should also indicate afflicted individuals. Thus, CP140 polypeptides and related reagents are useful in diagnosing sclerotic disease and in examining the role of CP140 in the development of scleroderma.

Use of CP140 Antibodies in Diagnosis Methods

CP140 antibodies can be used to screen patients for scleroderma by performing double-label immunofluorescence microscopy with patient sera samples. The basis of the test is detection of anti-CP140 autoantibodies in patient serum.

Cultured normal human cells, e.g., HeLa (liver) cells or HS27 human skin cells, are grown on glass coverslips, fixed, and permeabilized using standard techniques, e.g., using a 0.5% octoxynol detergent (e.g., TRITON X™-100, Rohm & Haas) buffer solution to wash the cells for 60 seconds. Various dilutions of sera from a patient (which may contain anti-CP140 autoantibodies) are mixed with CP140 sera raised in rabbits (anti-CP140 antibodies) and with the octoxynol detergent as described by Doxsey et al., *Cell*, 76:639–650 (1994). The resulting mixture is applied to the fixed cells.

After a one-hour incubation period, secondary antibodies coupled to fluorescent molecules are added to the cell sample to detect the anti-CP140 antibodies and human autoantibodies. Secondary antibodies coupled to different fluorophores, e.g., fluorescein or rhodamine, will specifically detect either human or rabbit IgG. Colocalization of fluorescence signals confirms that the signals are associated with centrosomes, and is thus scored as a positive signal. Sera from non-diseased individuals serve as controls. Statistical analysis of the data is performed, e.g., as described in Embury et al., *New England Journal of Medicine,* 316:656–659 (1987).

If a positive result is obtained in this assay, other diagnostic tests can be performed (see below). Positive results in both assay systems would provide strong evidence of scleroderma.

Use of Recombinant CP140 Polypeptide for Diagnosis

A second diagnostic test for scleroderma involves biochemical detection of a CP140 fragment or CP140 fragment-containing fusion protein. As above, the basis of the test is detection of anti-CP140 autoantibodies in a patient's serum.

In the second test, serial dilutions of a CP140 fragment fusion protein can be dotted onto nylon membranes (Immobilon, Schleicher and Schuell). Duplicate membranes are incubated with anti-CP140 antibodies and a serum sample from a patient. CP140 antibodies are used at defined concentrations, e.g., 2 µg/ml, as a positive control to ensure that the secondary antibodies work well, and different dilutions of the serum sample are used to ensure that a positive signal does not elude detection. Membranes are washed and probed with a secondary antibody that specifically bind to the anti-CP140 antibodies and the potential human autoimmune antibodies. The secondary antibodies are conjugated to alkaline phosphatase and reacted to detect enzymatic activity (Amersham). Quantitative data can be obtained using a highly sensitive PHOSPHORIMAGER™ (Analytics). Sera that give reactivity at least 3-fold higher than non-diseased (control) sera in two sets of samples are considered positive.

A CP140 polypeptide fragment, or a CP140 fragment-containing fusion protein, can also used to detect CP140 autoantibodies in a standard Western blot procedure. In such a procedure, a CP140 polypeptide fragment or CP140 fragment-containing fusion protein is subjected to SDS-polyacrylamide gel electrophoresis. It is then transferred ("blotted") onto a solid support such as Immobilon, and probed with human serum to be tested for CP140 autoantibodies. Detection of bound autoantibodies is typically by means of a secondary antibody linked to an enzyme such as alkaline phosphatase.

A CP140 polypeptide fragment, or a CP140 fragment-containing fusion protein, can also be used to detect CP140 autoantibodies in a conventional ELISA. In such a procedure, a CP140 polypeptide fragment, or a CP140 fragment-containing fusion protein is dried onto wells of a microtiter plate. Samples of appropriately diluted sera are added to the wells, and a secondary antibody linked to an enzyme such as alkaline phosphatase is used to detect binding of autoantibodies in serum samples to the immobilized CP140 polypeptide fragment. The amount of autoantibody present in a positive serum sample is readily quantitated by conventional methods.

Genetic Screening of Diseased Individuals

It is believed that anomalies in the CP140 gene are associated with scleroderma. DNAs obtained from sclerotic and normal (control) individuals are used in standard Polymerase Chain Reaction-Restriction Fragment Length Polymorphism (PCR-RFLP) assays as described in McPherson et al., *PCR, a Practical Approach,* Rickwood and Hames (eds.)(Oxford University Press, 1993). PCR is used to amplify portions of the CP140 gene in the sample DNA.

Figure 4:
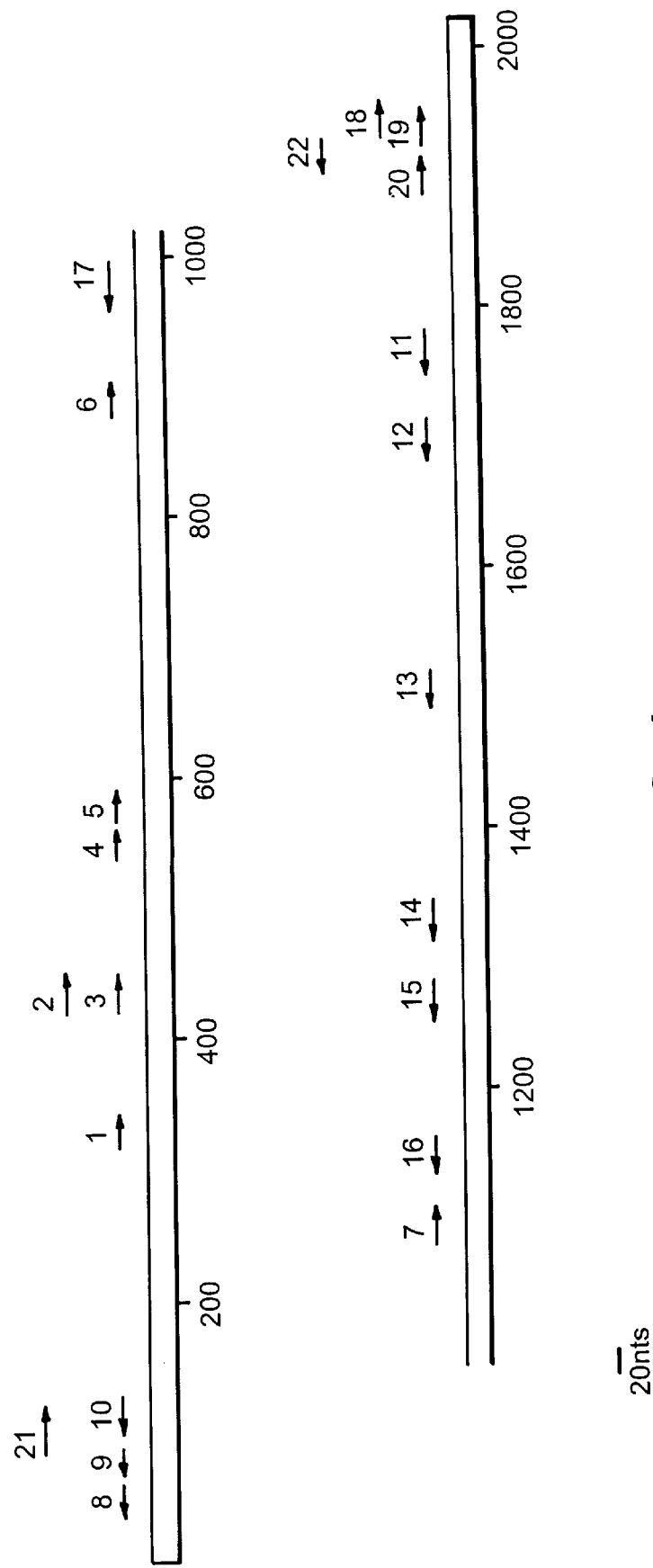
FIG. 4 is a schematic diagram depicting the orientation and approximate location of the oligonucleotide primers listed in FIG. 3, with respect to a CP140 cDNA.

FIG. 3 lists various oligonucleotide primers useful in the practice of the invention. FIG. 4 shows the location of the primers listed in FIG. 3 within the CP140 partial CDNA. FIG. 4 also shows the orientation of each primer.

Using FIGS. 3 and 4, it is within ordinary skill in the art to select a suitable pair of primers for PCR-RFLP assays, e.g., primer 1 for use as the 5' PCR primer, and primer 11 for use as the 3' PCR primer. Using the CP140 partial CDNA sequences, the skilled person can also design and use primers other than those listed in FIG. 3.

The DNA from potentially sclerotic individuals is compared by standard techniques to the human CP140 DNA obtained according to this invention, to detect any differences or variations as an indication of scleroderma.

Diseased and normal genes can be detected by conventional standard methods. Preferably, PCR is used to amplify a portion of the CP140 gene. PCR-amplified CP140 gene DNA fragments are digested with restriction enzymes to generate fragments of known length. Differences in the sizes of restriction fragments (polymorphisms) from diseased individuals reflect differences in the DNA sequences and represent genetic defects.

Such an analysis has been used successfully to detect abnormalities in other diseased genes (See, e.g., Embury et al., *New England J. Medicine,* 316:656–659, 1987). This approach may not detect all genetic defects. Therefore, other methods can be used to detect point mutations and minor deletions as outlined by McPherson et al., supra.

If genetic defects are identified in the DNA sample using these approaches, the PCR fragments containing the defective fragments are cloned (TA cloning kit, In Vitrogen) and sequenced to identify the altered site(s), e.g., as described in Doxsey et al., *Cell,* 76:639–650 (1994). This information is used to narrow the diagnostic screen to the abnormal fragment of the CP140 gene. The defect is mapped to the human chromosome and the characteristics of the genetic lesion can be compared to abnormalities in other known genetic disorders to determine whether the defect falls into known categories or has a characteristic pattern of other syndromes. Once the defective gene is characterized, it can be compared against the DNA obtained from patients, and thus used as a diagnostic tool.

CP140 mRNA Levels in Scleroderma Patients

The skin (and other epithelial tissues) of patients with scleroderma becomes thickened as the disease progresses. Since CP140 is involved in cell division, and division of epithelial cells in scleroderma patients appears to be altered, it is believed that the level of CP140 MRNA in individuals with scleroderma is different from the CP140 mRNA level in normal individuals. Thus, a different level of gene expression is an indication of the disease.

Skin fibroblasts (or other epithelial cells) are isolated from normal (control) and diseased individuals (see below) and assayed in reverse transcriptase-PCR (RT-PCR) as described in Chelly et al., *Nature (Lond.),* 333:858–860 (1988), to determine the amount of CP140 mRNA present in the cells. Briefly, RNA is isolated from these cells by standard procedures and RT is used to make cDNA from the RNA. The cDNA is then used for quantitative PCR analysis of the CP140 protein using actin as an internal control using standard techniques. The PCR probes described above also can be used for this assay. A change in normalized CP140 MRNA levels in cells from diseased individuals compared to normal individuals indicates the presence of disease. Appropriate normalization of data for meaningful comparisons is within ordinary skill in the art.

Expression of CP140 Protein in Scleroderma Patients

Skin fibroblasts (and other epithelial cells) can also be assayed for differences in the expression of CP140 protein in the diseased state. Cells are solubilized under denaturing conditions to liberate the centrosome-associated CP140. The protein is immunoprecipitated using antibodies and methods described above. Immunoprecipitates are exposed to SDS-PAGE to separate the proteins and are blotted onto nylon membranes. Membranes are probed with anti-CP140 antibodies and alkaline phosphatase secondary antibodies to detect the CP140 antibodies. Quantitative analysis is performed to detect differences in CP140 protein levels in diseased and normal cells using standard techniques. A substantial change in the level of CP140 protein in a sample indicates the presence of scleroderma.

Other Embodiments

The foregoing description is intended to illustrate and not to limit the scope of the invention, which is defined by the appended claims. Other embodiments are within the following claims.

What is claimed is:

1. A diagnostic method for screening a patient for the presence of anti-CP140 autoantibodies as an indication of sclerotic disease, said method comprising the steps of:

(a) obtaining a biological sample from the patient;

(b) obtaining a substantially pure CP140 polypeptide fragment;

(c) contacting said sample with said CP140 polypeptide fragment under conditions that allow said CP140 fragment to bind to anti-CP140 autoantibodies; and (d) detecting autoantibody:CP140 complexes, if present, as an indication of the presence of sclerotic disease in the patient.

2. The method of claim 1, wherein said contacting step and said detecting step are part of an ELISA procedure.

3. The method of claim 1, wherein said substantially pure CP140 polypeptide fragment is part of a fusion protein.

4. The method of claim 3, wherein said fusion protein comprises a glutathione-S-transferase moiety.

5. The method of claim 1, wherein said contacting step and said detecting step are part of a Western blot procedure.

6. A method for screening a patient for the presence of anti-CP140 autoantibodies as an indication of sclerotic disease, said method comprising the steps of:

(a) obtaining a culture of non-sclerotic human cells that contain CP140;

(b) permeabilizing said non-sclerotic human cells to allow entry of antibodies into the cells;

(c) obtaining a serum sample from said patient;

(d) contacting said sample with the permeabilized cells;

(e) contacting with the permeabilized cells a purified anti-CP140 antibody;

(f) contacting the permeabilized cells with secondary antibodies to detect any anti-CP140 autoantibodies and anti-CP140 antibody bound in steps (d) and (e), wherein the secondary antibodies to detect anti-CP140 autoantibodies and to detect anti-CP140 antibody are coupled to different first and second fluorescent labels;

(g) detecting cells that contain co-localized first and second labels, wherein cells having colocalized first and second labels are an indication of the presence of sclerotic disease in said patient.

7. The method of claim 6, wherein said secondary antibody to detect anti-CP140 autoantibodies.

8. The method of claim 6, wherein said secondary antibody to detect anti-CP140 antibody is an anti-rabbit IgG antibody.

9. A method for screening a patient for altered CP140 protein level as an indication of sclerotic disease, said method comprising the steps of:

(a) obtaining a sample of cells from a patient; and (b) detecting a change in the quantity of CP1140 in said cells compared to the quantity of CPl40 in a sample of non-sclerotic cells, as an indication of the presence of sclerotic disease in said patient.

10. The method of claim 9, wherein said detecting is by means of a CP140-specific antibody.

* * * * *